US006551992B1

(12) United States Patent
DeFelippis et al.

(10) Patent No.: US 6,551,992 B1
(45) Date of Patent: *Apr. 22, 2003

(54) STABLE INSULIN FORMULATIONS

(75) Inventors: Michael Rosario DeFelippis, Indianapolis, IN (US); Michael Allen Dobbins, Lebanon, IN (US); Bruce Hill Frank, Indianapolis, IN (US); Shun Li, Indianapolis, IN (US); Dawn Marie Rebhun, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/450,794

(22) Filed: Nov. 29, 1999

Related U.S. Application Data

(62) Division of application No. 09/096,247, filed on Jun. 11, 1998, now Pat. No. 6,034,054.
(60) Provisional application No. 60/053,089, filed on Jun. 13, 1997.

(51) Int. Cl.[7] .......................... A61K 38/28; A61K 38/00
(52) U.S. Cl. .............................. 514/3; 514/866; 514/4; 530/303; 530/304; 530/300
(58) Field of Search ................................ 530/303, 304, 530/305, 300, 324; 514/3, 4, 12

(56) References Cited

U.S. PATENT DOCUMENTS

| 4,472,385 A | 9/1984 | Brange et al. ............... 424/178 |
| 4,476,118 A | 10/1984 | Brange et al. ............... 424/178 |
| 4,783,441 A | 11/1988 | Thurow .......................... 514/3 |
| 4,839,341 A | 6/1989 | Massey et al. .................. 514/4 |
| 5,461,031 A | 10/1995 | DeFelippis ..................... 514/4 |
| 5,474,978 A | 12/1995 | Bakaysa et al. ................ 514/4 |
| 5,514,646 A | 5/1996 | Chance et al. .................. 514/3 |
| 5,547,929 A | 8/1996 | Anderson et al. ............... 514/3 |
| 5,650,486 A | 7/1997 | DeFelippis .................. 530/305 |
| 5,658,878 A | 8/1997 | Backstrom et al. ............. 514/3 |

FOREIGN PATENT DOCUMENTS

| EP | 214 826 | 3/1987 |
| EP | 0 735 048 A | 2/1996 |
| GB | 1285023 | 8/1972 |
| WO | WO 87/06137 | 10/1987 |
| WO | WO 99/34821 | 7/1999 |

OTHER PUBLICATIONS

Markussen Jan, Damgaard U, Jørgensen KH, Sørensen, Thim L "Human Monocomponent Insulin", Acta. Med. Scand., Suppl., No. 671, pp. 99–105, 1983.
J. Brange, et al., "Chemical stability of insulin", *Aeta Pharm. Nord.* 4(3) 149–158 (1992).
R. Quinn, et al., "Minimizing the aggregation of neutral insulin solutions", *Journal of Pharmaceutical Sciences* vol. 72, No. 12, Dec. 1983.
Brems, et al., *Protein Engineering*, 6:527–533 (1992).
Brange, et al., *Current Opinion in Structural Biology*, 1:934–940 (1991).
Patent Abstract of Japan, vol. 006, No. 143, C–117, Aug. 3, 1982 & JP 57 067548 A (Shionogi & Co Ltd), Apr. 24, 1982, refers to preparation comprising insulin analogues in the presence of glycerine, trishydroxy–methylaminomethane, ZnC12 and cresol–phenol as an antiseptic.

*Primary Examiner*—Christopher S. F. Low
(74) *Attorney, Agent, or Firm*—Grant E. Reed; Mark J. Stewart

(57) ABSTRACT

The present invention provides a monomeric insulin analog formulation stabilized against aggregation in which the buffering agent is either TRIS or arginine. The stable formulations of the present invention are useful for treating diabetes, and are particularly advantageous in treatment regimes requiring lengthy chemical and physical stability, such as, in continuous infusion systems.

23 Claims, No Drawings

STABLE INSULIN FORMULATIONS

CROSS-REFERENCE

This application is a divisional application of U.S. Ser. No. 09/096,247, filed on Jun. 11, 1998 now U.S. Pat. No. 6,034,054 which claims the benefit of U.S. Provisional Application No. 60/053,089, filed Jun. 13, 1997 now abandoned.

BACKGROUND OF THE INVENTION

The present invent on is in the field of human medicine, particularly in the treatment of diabetes and hyperglycemia by the administration of monomeric insulin analogs. More specifically, the present invention relates to formulations of monomeric insulin analogs that have superior long-term physical stability when exposed to high mechanical energy input and high temperature.

Stable formulations of therapeutic agents are particularly required for use in delivery devices that expose these agents to elevated temperatures and/or mechanical stress. For example, stable insulin formulations are required for use in continuous infusion systems and pen delivery devices. Current formulations provide only limited stability in these types of delivery devices.

In continuous infusion systems, a fluid containing a therapeutic agent is pumped from a reservoir, usually to a subcutaneous, intravenous, or intraperitoneal depot. The reservoir, which must be refilled periodically, is attached to the patient's body, or is implanted in the patient's body. In either case, the patient's body heat and body motion, plus turbulence in the tubing and pump impart a relatively high amount of thermo-mechanical energy to the formulation. In the interest of minimizing the frequency with which the reservoir is refilled, and of minimizing the size of the reservoir, formulations having a relatively high concentration of the therapeutic agent are highly advantageous.

Massey and Sheliga, U.S. Pat. No. 4,839,341 (Eli Lilly and Company, 1989) discuss the challenges involved in providing stable insulin formulactions for continuous infusion, and present a thorough review of the art through about 1984. The challenges are even greater at the present time because insulin formulations that are stable for 1 to 3 months are now demanded.

Injector pens have also been developed to aid diabetics in measuring and administering an accurate and controlled dose of insulin. Generally, these pens are secured onto a cartridge having a particular quantity of liquid medication sealed therein. The cartridge includes a plunger and a mechanism for advancing the plunger in the cartridge in such a manner to dispense the medication. Injector pens may be reusable or disposable. In reusable pens, a user can change a spent cartridge and reset the leadscrew of the pen back to its initial position. In a disposable pen, the cartridge is permanently captured in the pen which is disposed of after the contents of the cartridge have been exhausted. Formulations of insulin used in these pens are exposed to physical stress and limited stability is usually observed.

With the introduction of new monomeric insulin analogs for the treatment of diabetes, there is a need to utilize these compounds in treatment regimes that can compromise the inherent stability of the formulations. Rapid-acting insulins, known as monomeric insulin analogs, are well-known in the art, and are disclosed in Chance, et al. U.S. Pat. No. 5,514,646, issued May 7, 1996; Brems, et al., *Protein Engineering*, 6:527–533 (1992); Brange, et al., EPO publication No. 214,826 (published March 18, 1987); and Brange, et al., *Current Opinion in Structural Biology* 1:934–940 (1991). Monomeric insulin analogs are absorbed much faster than is insulin, and are ideally suited for postprandial control of blood glucose levels in patients in need thereof. They are also specially well-suited for administration by continuous infusion for both prandial and basal control of blood glucose levels because of their rapid absorption from the site of administration.

Unfortunately, monomeric insulin analog formulations have a propensity to aggregate and to become unstable when exposed to thermo-mechanical stress [Bakaysa, et al., U.S. Pat. No. 5,474,978, issued Dec. 12, 1995]. Aggregation may even be manifested as precipitation of higher-order insulin species. In this way, aggregation can prevent reproducible delivery of effective therapeutic doses of monomeric insulin analogs, and may also cause irritation at the administration site or a more systemic immunological response. Insulin analog formulations stabilized against aggregation are desirable.

Formulations of monomeric insulin analogs for use in continuous infusion systems must remain soluble and substantially free of aggregation, even though subjected to the patient's body heat and motion for periods ranging from a few days to several months. Instability is promoted by the higher protein concentrations that are desirable for continuous infusion systems and by the thermo-mechanical stress to which formulations are exposed in continuous infusion systems. Therefore, improvement in the physical and chemical stability of concentrated insulin analog formulations is urgently needed to permit them to be used successfully in continuous infusion systems. Improvement in the stability of monomeric insulin formulations for uses other than in continuous infusion is also beneficial.

Stabilized formulations of monomeric insulin analogs that are fast-acting, are known. Bakaysa, et al., U.S. Pat. No. 5,474,978 disclose and claim a human insulin analog complex comprising six molecules of a human insulin analog (hexamer complex), two zinc atoms, and at least three molecules of a phenolic preservative, formulations comprising the hexamer complex, and methods of treating diabetes mellitus by administering the formulation. Bakaysa, et al., also claim formulations of the hexamer complex further comprising an isotonicity agent and a physiologically tolerated buffer.

The specification of U.S. Pat. No. 5,474,978 discloses that the zinc complexes of monomeric insulin analogs may be formulated in the presence of a "physiologically tolerated buffer." Among the buffers mentioned for use in formulations are sodium phosphate, sodium acetate, sodium citrate, and TRIS. The examples in U.S. Pat. No. 5,474,978 only describe formulations wherein the buffer is sodium phosphate, and only sodium phosphate buffer is required in a claim (Claim 5). None of the examples in U.S. Pat. No. 5,474,978 specifically disclose the use of TRIS buffer in formulations of zinc-monomeric insulin analog complexes.

Monomeric insulin analog formulations containing protamine have also been developed to yield, upon use, an intermediate duration of action. Monomeric insulin analog-protamine formulations are described in U.S. Pat. No. 5,461,031. Methods for crystallizing monomeric insulin analogs with the basic peptide protamine to yield a neutral protamine suspension are known in the art. In addition, biphasic mixtures containing a monomeric insulin analog solution and a monomeric insulin analog-protamine suspenion can be prepared. These mixture have the optimal time-action properties of the analogue in combination with basal activity. Monomeric insulin analog mixtures are also described in U.S. Pat. No. 5,461,031.

Monomeric insulin analog-protamine suspension formulations and biphasic mixtures are suitable for use in cartridge container presentations. Yet, because these devices require frequent patient manipulation, increased stress to the preparation results. Protamine salt formulations in particular have limited stability when exposed to thermomechnical stress. Thus, there is a need to develop stable intermediate acting monomeric insulin analog-protamine formulations as well as biphasic mixture formulations.

We have now discovered that when certain physiologically tolerated buffers other than phosphate are employed in formulations of zinc-monomeric insulin analog complexes, protamine salt formulations, or biphasic mixtures of monomeric insulin analog, the physical stability of the formulations is unexpectedly and considerably greater than when phosphate buffer is used. Most advantageous is our discovery that, whereas, soluble formulations of zinc-monomeric insulin analog complexes with a phosphate buffer, such as those specifically exemplified in U.S. Pat. No. 5,474,978, are not physically stable enough for long-term administration using continuous infusion pumping systems, the soluble formulations provided by the instant invention are sufficiently stable to be used with safety for long periods of insulin infusion. We have also discovered that the addition of arginine to protamine salt formulations of monomeric insluin analogs results in dramatic improvements in both the chemical and physical stability of the formulation.

SUMMARY OF THE INVENTION

Accordingly, the instant invention provides a solution formulation comprising a physiologically-tolerated buffer selected from the group consisting of TRIS and arginine; a monomeric insulin analog; zinc; and a phenolic preservative.

The invention also encompasses an insulin analog formulation comprising a monomric insulin analog; zinc; a phenolic preservative; protamine; and a buffer selected from the group consisting of TRIS and arginine.

The invention further provides methods of using the insulin analog formulation to treat diabetes and hyperglycemia in a patient indeed thereof, which comprises administering to the patient a stable formulation of the present invention.

DETAILED DESCRIPTION AND PREFERRED EMBODIMENTS

For purposes of the present invention, as disclosed and claimed herein, the following terms and abbreviations have the following meanings.

The term "administer" means to introduce a formulation of the present invention into the body of a patient in need thereof to treat a disease or condition.

The various forms of the verb "to aggregate" refer to a process whereby individual molecules or complexes associate to form aggregates. An aggregate is a polymeric assembly comprising molecules or complexes of monomeric insulin analog. For the purpose of the present invention, the monomeric insulin analog hexamer is not an aggregate, but a complex. Monomeric insulin analogs, and hexamer complexes thereof, have a propensity to aggregate when exposed to thermo-mechanical stress. Aggregation can proceed to the extent that a visible precipitate is formed.

The term "arginine" refers to the amino acid and encompasses the D- and L-enantiomers as well as mixtures thereof. The term also includes any pharmacologically acceptable salts thereof. Arginine is also known in the art as 1-amino-4-guanidinovaleric acid. Arginine readily forms salts, such as the hydrochloride salt.

The term "complex" means a compound in which a transition metal is coordinated to at least one ligand. Ligands include nitrogen-containing molecules, such as proteins, peptides, amino acids, and TRIS, among many other compounds. Monomeric insulin analog can be a ligand of divalent zinc ions.

The term "continuous infusion system" refers to a device for continuously administering a fluid to a patient parenterally for an extended period of time or for intermittently administering a fluid to a patient parenterally over an extended period of time without having to establish a new site of administration each time the fluid is administered. The fluid contains a therapeutic agent or agents. The device comprises a reservoir for storing the fluid before it is infused, a pump, a catheter, or other tubing for connecting the reservoir to the administration site via the pump, and control elements to regulate the pump. The device may be constructed for implantation, usually subcutaneously. In such a case, the insulin reservoir will usually be adapted for percutaneous refilling. Obviously, when the device is implanted, the contents of the reservoir will be at body temperature, and subject to the patient's body motion.

An "isotonicity agent" is a compound that is physiologically tolerated and imparts a suitable tonicity to a formulation to prevent the net flow of water across cell membranes that are in contact with the formulation. Compounds, such as glycerin, are commonly used for such purposes at known concentrations. Other possible isotonicity agents include salts, e.g., sodium chloride, dextrose, and lactose.

The terms "monomeric human insulin analog" "monomeric insulin analog" and "human insulin analog" are well-known in the art, and refer generally to fast-acting analogs of human insulin, which include:

human insulin, wherein Pro at position B28 is substituted with Asp, Lys, Leu, Val, or Ala, and wherein position B29 is Lys or is substituted with Pro;

AlaB26-human insulin des(B28–B30) human insulin; and des(B27) human insulin.

Such monomeric insulin analogs are disclosed in Chance, et al., U.S. Pat. No. 5,514,646, issued May 7, 1996; Chance, et al., U.S. patent application Ser. No. 08/255,297; Brems, et al., *Protein Engineering*, 6:527–533 (1992); Brange, et al., EPO publication No. 214,826 (published Mar. 18, 1987); and Brange, et al., *Current Opinion in Structural Biology* 1:934–940 (1991). The monomeric insulin analogs employed in the present formulations are properly cross-linked. A properly cross-linked insulin analog contains three disulfide bridges: one between position 7 of the A-chain and position 7 of the B-chain, a second between position 20 of the A-chain and position 19 of the B-chain, and a third between positions 6 and 11 of the A-chain.

The term "phenolic preservative" as used herein refers to chlorocresol, m-cresol, phenol, or mixtures thereof.

As used herein, the noun "stability" refers to the physical stability of formulations of monomeric insulin analogs. Physical instability of a protein formulation may be caused by aggregation of the protein molecules to form higher order polymers or even precipitates. A "stable" formulation is one wherein the degree of aggregation of proteins therein is acceptably controlled, and does not increase unacceptably with time. Monomeric insulin analog formulations have a propensity to aggregate when exposed to thermo-mechanical stress. Physical stability may be assessed by methods well-known in the art, including measurement of a sample's apparent attenuation of light (absorbance, or optical density). Such a measurement of light attenuation relates to the turbidity of a formulation. Turbidity is produced by aggregation or precipitation of proteins or complexes in the formulation. Other methods for assessing physical stability are well-known in the art.

The term "treating" refers to the management and care of a patient having diabetes or hyperglycemia, or other condition for which insulin administration is indicated for the purpose of combating or alleviating symptoms and complications of those conditions. Treating includes administering a formulation of present invention to prevent the onset of the symptoms or complications, alleviating the symptoms or complications, or eliminating the disease, condition, or disorder.

The term "TRIS" refers to 2-amino-2-hydroxymethyl-1, 3,-propanediol, and to any pharmacologically acceptable salt thereof. The free base and the hydrochloride form are two common forms of TRIS. TRIS is also known in the art as trimethylol aminomethane, tromethamine, and tris (hydroxymethyl)aminomethane.

That the instant invention provides formulations of monomeric insulin analogs having greatly increased physical stability relative to those known in the art will be readily appreciated from the following data.

Formulations comprising a monomeric insulin analog, $Lys^{B28}Pro^{B29}$-Human Insulin Analog, and TRIS, prepared essentially as described in Example 3 herein, were subjected to accelerated stability testing as described below. Samples of the prepared formulations were placed into pre-cleaned, 2 mL capacity, glass HPLC autosampler vials. Each vial contained three Teflon® balls approximately 3/16 inch in diameter. Air was completely displaced from the vial by the sample of formulation. After sealing, the vials were continuously shaken at 40 Hz (20×g, average linear acceleration at a peak-to-peak amplitude of 12 mm, and at 37° C. to provide a relatively high level of mechanical energy input to the formulations at a temperature that favors aggregation and physical instability. The vials were positioned on the shaker such that their long dimension (i.e., top to bottom) was oriented parallel to the direction of linear acceleration— that is, they lay on their sides on the surface of the shaker. It has been shown for insulin formulations that increased stability under the accelerated conditions described above correlates with greatly increased in-use stability.

The optical density at 450 nm of sample formulations and of control formulations was measured periodically using a Shimadzu 1201 spectrophotometer. Control formulations were prepared in the same manner as sample formulations, but were stored at 4° C. without agitation. The net optical density was calculated for a sample by subtracting the optical density of the control from the optical density of the sample. Values in Table 1 are the average net optical density and standard deviation for the number of samples (n) given. Sample and control formulations containing phosphate as the buffer (pH 7.4±0.1) were prepared essentially is described in Example 4.

TABLE 1

Effects of Buffer and Time of Exposure to High Mechanical Energy Input at 37° C. on the Turbidity (Optical Density at 450 nm) of Formulations of $Lys^{B28}Pro^{B29}$-Human Insulin Analog

| | Optical Density at 45U nm | | | |
|---|---|---|---|---|
| | 16 hours | 70 hours | 100 hours | 500 hours |
| Example 3 (TRIS) | 0.02 ± 0.01 n = 5 | 0.03 ± 0.02 n = 5 | 0.01 ± 0.01 n = 5 | 0.04 ± 0.01 n = 4 |
| Example 4 (Phosphate) | 0.81 ± 0.71 n = 5 | N.D. | N.D. | N.D. |

N.D. = not determined

Under the conditions described above, turbidity in the formulations having a phosphate buffer reached very high, and unacceptable levels by 16 hours (Table 1, Example 4) compared with control formulations containing phosphate that were stored at 4° C. without agitation. On the other hand, the optical density of formulations having TRIS as the buffer remained virtually the same as the optical density in the control for 500 hours for formulations containing TRIS (Example 3). The data in Table 1 clearly demonstrate that replacement of phosphate buffer with TRIS buffer in formulations of $Lys^{B28}Pro^{B29}$-Human Insulin Analog drastically increases the stability of the formulations. Based on observations with other insulin formulations, it is believed that the surprising and significant stability of formulations of monomeric insulin analog in TRIS buffer in the accelerated test will translate into "in-use" stability far greater than 500 hours because the energy input is greater in the accelerated test than during expected uses.

Formulations comprising a monomeric insulin analog, $Lys^{B28}Pro^{B29}$-Human Insulin Analog, and either TRIS, phosphate, or L-arginine as buffers were prepared essentially as described in Examples 3, 4, and 5, respectively. Three lots of $Lys^{B28}Pro^{B29}$-Human Insulin Analog were used to prepare the formulations. For each combination of analog lot and buffer, six samples were subjected to stability testing as described above. Four different shakers were used to impart mechanical energy to the vials. Each shaker had at least one sample of each lot and buffer combination. Stability of the formulations was assessed periodically by measuring the optical density of samples and controls as described above. Results are in Table 2. Values in Table 2 are the average net optical density and standard deviation of six samples for each lot and buffer.

TABLE 2

Effects of Buffer, Lot of Analog, and Time of Exposure to High Mechanical Energy Input at 37° C. on the Turbidity (Optical Density at 450 nm) of Formulations of $Lys^{B28}Pro^{B29}$-Human Insulin Analog

| | Analog | Optical Density at 450 nm | | | |
|---|---|---|---|---|---|
| Buffer | Lot | 23 hours | 47 hours | 87 hours | 139 hours |
| TRIS | Lot 1 | 0.02 ± 0.02 | 0.06 ± 0.02 | 0.05 ± 0.02 | 0.00 ± 0.02 |
| | Lot 2 | 0.00 ± 0.01 | 0.04 ± 0.02 | 0.03 ± 0.01 | 0.00 ± 0.02 |
| | Lot 3 | 0.02 ± 0.02 | 0.05 ± 0.03 | 0.04 ± 0.03 | 0.01 ± 0.02 |

TABLE 2-continued

Effects of Buffer, Lot of Analog, and Time of
Exposure to High Mechanical Energy Input at 37° C. on the
Turbidity (Optical Density at 450 nm) of Formulations of
Lys$^{B28}$Pro$^{B29}$-Human Insulin Analog

| Buffer | Analog Lot | Optical Density at 450 nm | | | |
|---|---|---|---|---|---|
| | | 23 hours | 47 hours | 87 hours | 139 hours |
| Arginine | Lot 1 | 0.01 ± 0.02 | 0.04 ± 0.02 | 0.04 ± 0.02 | 2.12 ± 1.03 |
| | Lot 2 | 0.01 ± 0.02 | 0.04 ± 0.02 | 0.06 ± 0.08 | 1.80 ± 0.60 |
| | Lot 3 | 0.00 ± 0.02 | 0.03 ± 0.02 | 1.84 ± 0.66 | N.D. |
| Phosphate | Lot 1 | 0.13 ± 0.06 | 2.68 ± 0.17 | 2.61 ± 0.11 | N.D. |
| | Lot 2 | 0.21 ± 0.24 | 2.14 ± 0.75 | 2.75 ± 0.14 | N.D. |
| | Lot 3 | 0.29 ± 0.23 | 2.75 ± 0.14 | 2.79 ± 0.11 | N.D. |

Under the conditions described above, turbidity in the formulations having a phosphate buffer reached very high, and unacceptable levels by 23 hours, regardless of the lot of insulin analog used (Table 2). By contrast, turbidity in formulations having TRIS as the buffer remained essentially unchanged for 139 hours, regardless of the lot of insulin used. Formulations containing L-arginine buffer demonstrated better physical stability compared with formulations containing phosphate, and the duration of their stability depended somewhat on the lot of insulin analog used. The data in Table 2 clearly demonstrate that formulations of Lys$^{B28}$Pro$^{B29}$-Human Insulin Analog comprising TRIS buffer or L-arginine buffer at pH 7.4 remain stable against aggregation for markedly longer periods of time than do formulations comprising a phosphate buffer. Again, it is believed that the surprising and significant stability of formulations of monomeric insulin analog in TRIS and in L-arginine buffer will translate into "in-use" stability far greater than observed in the accelerated test because the energy input is greater in the accelerated test than during expected uses.

Susceptibility to changes in morphology and appearance for Lys$^{B28}$Pro$^{B29}$ suspension formulations were evaluated by the Physical Stability Stress Test (PSST). In this thermomechanical method, preparations were sealed with no headspace in a fixed volume container with a glass bead. The containers were placed in a chamber at elevated temperature (approximately 37 degrees C.), rotated at a fixed speed (about 30 rpm) for a defined time (about 4 hours) and then held quiescent for the remainder of a 24 hour period. Containers were evaluated for changes and removed from testing when it was determined that aggregation (clumping) had occurred. Longer periods on test without a failure, as well as larger numbers of containers remaining on test, were equated with increased physical stability.

Two different mixture containing Lys$^{B28}$Pro$^{B29}$ and Lys$^{B28}$Pro$^{B29}$-protamine crystals were tested. The ratio of Lys$^{B28}$Pro$^{B29}$ to Lys$^{B28}$Pro$^{B29}$protamine for the low mixture was 25:75 and for the high mixture was 75:25. The mixtures were prepared as described in Examples 6 and 7. When the low mixture was tested using th PSST method, only formulations containing arginine had containers remaining after 18 days. Two of the test samples had containers remaining out to 44 days. The PSST on high mixtures showed similar results with the formulations containing arginine having approximately 50% of the containers remaining after 36 days of testing whereas the control formulations containing phosphate buffer had 0 to 5% of the containers remaining after 36 days.

Preferred monomeric insulin analogs for use in the formulations of the present invention are Lys$^{B28}$Pro$^{B29}$-human insulin, Asp$^{B28}$-human insulin, and Ala$^{B26}$-human insulin.

The concentration of monomeric insulin analog in the present formulations ranges from 1.2 mg/mL to 50 mg/mL. A preferred range of analog concentration is from about 3.0 mg/mL to about 35 mg/mL. More preferred concentrations are about 3.5 mg/mL, about 7 mg/mL, about 14 mg/mL, about 17.5 mg/mL, and about 35 mg/mL which correspond approximately to formulations having about 10 units, about 200 units, about 400 units, about 500 units, and about 1000 units of insulin activity per mL, respectively.

The concentration of zinc in the formulations ranges from about 4.5 mg/mL to about 370 mg/mL, and must be such that at least two zinc atoms are available to complex with the six insulin molecules in each hexamer. The ratio of total zinc (complexed zinc plus uncomplexed zinc) to insulin analog hexamer should be between 2 and 4. A ratio of about 3 to about 4 atoms of total zinc per insulin analog hexamer complex is preferred.

The minimum concentration of phenolic preservative that is required to form the monomeric insulin analog hexamer in the present formulations. For some purposes, such as to meet compendial preservative effectiveness requirements for multi-use formulations, the concentration of phenolic preservative in the present formulations may be increased above that required to form hexamers to an amount necessary to maintain preservative effectiveness. The concentration of preservative necessary for effective preservation depends on the preservative used, the pH of the formulation, and whether substances that bind or sequester the preservative are also present. Generally, the amount necessary can be found in, e.g., Wallhauser, K. DH. Develop. Biol. Standard. 24, pp. 9–28 (Basel, S. Krager, 1974). When formulated, the insulin analog hexamer complex used in the present formulation binds as many as seven phenolics, though generally, only six. phenolics are bound to the hexamer. A minimum of about three phenolics is required for hexamer formation. When preservative is required for antimicrobial effectiveness, the preferred phenolic concentration is about 23 mM to about 35 mM. M-cresol and phenol, either separately or in mixtures, are preferred preservatives.

The formulations may optionally contain an isotonicity agent. The formulations preferably contain an isotonicity agent, and glycerin is the most preferred isotonicity agent. The concentration of glycerin, when it is used, is in the range known in the art for insulin formulations, preferably about 16 mg/mL.

The pH of the formulations is controlled by a buffering agent, such as TRIS or L-arginine. The concentration of the buffers is not thought to play a critical role in obtaining the object of the invention, and should be such as to provide adequate buffering of the pH during storage to maintain the pH at a target pH ±0.1 pH unit. The preferred pH is between about 7 and about 8, when measured at a temperature of about 22° C.

Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) may optionally be added to the formulation. These additives are not required to achieve the great advantage of the present invention, but may be useful if the formulations will contact plastic materials.

The present invention also encompasses protamine salt preparations with varying proportions of soluble fractions of monomeric insulin analogs. No specific conformational requirements of the insulin molecule are required to stabilize the formulation with arginine, although excipients like zinc and preservatives normally added to insulin formulation (discussed above) may work in concert with arginine to enhance stabilization. Arginine concentrations range from 1 to 100 mM in formulations containing protamine. Most preferred is an arginine concentration range of 5 to 25 mM. Arginine can be added as a supplement to solutions or precipitated suspensions already containing zinc ions and phenolic preservatives.

Administration may be via any route known to be effective by the physician of ordinary skill. Parenteral administration is preferred. Parenteral administration is commonly understood as administration by other than a gastrointestinal route. Preferred parenteral routes for administering the formulations of the present invention include intravenous, intramuscular, subcutaneous, intraperitoneal, intraarterial, nasal, pulmonary, and buccal routes. Intravenous, intraperitoneal, intramuscular, and subcutaneous routes of administration of the compounds used in the present invention are more preferred parenteral routes of administration. Intravenous, intraperitoneal, and subcutaneous routes of administration of the formulations of the present invention yet more highly preferred.

Administration via certain parenteral routes may involve introducing the formulations of the present invention into the body of a patient through a needle or a catheter, propelled by a sterile syringe or some other mechanical device such as an continuous infusion system. A formulation provided by the present invention may be administered using a syringe, injector, pump, or any other device recognized in the art for parenteral administration. A formulation of the present invention may also be administered as an aerosol for absorption in the lung or nasal cavity. The formulations may also be administered for absorption through the mucus membranes, such as in buccal administration.

The amount of a formulation of the present invention that is administered to treat diabetes or hyperglycemia depends on a number of factors, among which are included, without limitation, the patient's sex, weight and age, the underlying causes of the condition or disease to be treated, the route of administration and bioavailability, the persistence of the administered monomeric insulin analog in the body, the formulation, and the potency of the monomeric insulin analog. Where administration is intermittent, the amount per administration should also take into account the interval between doses, and the bioavailability of the monomeric insulin analog from the formulation. Administration of the formulation of the present invention could be continuous. It is within the skill of the ordinary physician to titrate the dose and infusion rate or frequency of administration of the formulation of the present invention to achieve the desired clinical result.

Monomeric insulin analogs used in the present invention can be prepared by any of a variety of recognized peptide synthesis techniques including classical solution methods, solid phase methods, semi-synthetic methods, and recombinant DNA methods. Chance, et al., U.S. Pat. No. 5,514, 646, issued May 7, 1996, discloses the preparation of various monomeric insulin analogs with sufficient detail to enable one skilled in the art to prepare any of the monomeric insulin analogs used in the present invention.

Both zinc and a phenolic preservative are essential to achieve a complex that is stable and capable of rapid dissociation and onset of action. The hexamer complex consists of two zinc ions per hexamer of human insulin analog, and at least three molecules of a phenolic preservative selected from the group consisting of chlorocresol, m-cresol, phenol, and mixtures thereof.

Soluble monomeric insulin analog is converted to the hexamer complex by dissolving the monomeric insulin analog in a diluent containing the phenolic preservative in suitable quantities at a pH of about 7 to about 8 and then adding zinc. Zinc is preferably added as a zinc salt, such as, without limitation, zinc acetate, zinc bromide, zinc chloride, zinc fluoride, zinc iodide, and zinc sulfate. The skilled artisan will recognize that there are many other zinc salts which also might be used to make the monomeric insulin analog complexes that are part of the present invention. Preferably, zinc acetate, zinc oxide, or zinc chloride is used because those compounds do not add new chemical ions to commercially accepted processes.

Dissolution of th monomeric insulin analog may be aided by what is commonly known as "acid dissolution." For acid dissolution, the pH the aqueous solvent is lowered to about 3.0 to 3.5 with a physiologically tolerated acid, preferably HCl, to aid in the dissolution of the monomeric analog. Other physiologically tolerated acids include, without limitation, acetic acid, citric acid, and sulfuric acid. Phosphoric acid is preferably not used to adjust pH in preparing the formulations of the present invention. The pH is then adjusted with a physiologically tolerated base, preferably sodium hydroxide, to about pH 7.3 to 7.5. Other physiologically tolerated bases include, without limitation, potassium hydroxide and ammonium hydroxide. Thereafter, the phenolic preservative and zinc are added.

Parenteral formulations of the present invention can be prepared using conventional dissolution and mixing procedures. To prepare a suitable formulation, for example, a measured amount of monomeric insulin analog in water is combined with the desired preservative, a zinc compound, and the buffering agent, in water in sufficient quantities to prepare the hexamer complex. The formulation is generally sterile filtered prior to administration. Variations of this process would be recognized by one of ordinary skill in the art. For example, the order the components are added, the order in which pH is adjusted, if any, the temperature and ionic strength at which the formulation is prepared, may be optimized for the concentration and means of administration used.

The following examples and preparations are provided merely to further illustrate the preparation of the formulations of the invention. The scope of the invention is not limited to the following examples.

EXAMPLE 1

Preparation of a U100 Soluble Formulation Containing $Lys^{B28}Pro^{B29}$-Human Insulin Analog and TRIS An amount of $Lys^{B28}Pro^{B29}$-Human Insulin Analog-Zinc Crystals calculated to yield 100 Units of insulin activity per milliliter in he final formulation were suspended in an aqueous solution containing 0.715 mg/mL phenol, 1.76 mg/mL m-cresol 16 mg/mL glycerin, and zinc oxide. The insulin analog-zinc crystals contained about 0.36% zinc on a weight basis. The concentration of zinc oxide in the aqueous diluet was such as to supplement the final zinc ion concentration of the formulation to about 0.025 mg per 100 units of insulin activity. A volume of 10% hydrochloric acid was added to adjust the pH to 2.8 to 3.0. After stirring to dissolve the crystals, aliquots of 10% sodium hydroxide solution were carefully added to adjust the pH to 7.4 to 7.7. A volume of a stock solution of TRIS (50 g/mL, pH 7.4, measured at ambient temperature, i.e., about 2° C.) calculated to give a concentration of TRIS of 2 mg/mL in the final formulation, was added to the insulin analog solution water was added to dilute the formulation to the final volume. The formulation was sterile-filtered using a 0.2 micron filter.

EXAMPLE 2

Preparation of a U100 Soluble Formulation Containing $Lys^{B28}Pro^{B29}$-Human Insulin Analog and L-Arginine The process described in Example 1 was followed until addition of the buffer. Then, instead of adding a volume of a TRIS stock solution, a volume of a stock solution of L-arginine (200 mM, pH 7.4), calculated to give a concentration of L-arginine of 20 mM in the final formulation, was added to the insulin analog solution. Water was added to dilute the formulation to the final volume. The formulation was sterile-filtered using a 0.2 micron filter.

EXAMPLE 3

Preparation of a U400 Soluble Formulation Containing $Lys^{B28}Pro^{B29}$Human Insulin Analog and TRIS An amount of $Lys^{B28}Pro^{B29}$-Human Insulin Analog-Zinc Crystals calculated to yield 400 Units of insulin activity per milliliter in the final formulation were suspended in an aqueous solution containing 0.715 mg/mL phenol, 1.76 mg/mL m-cresol 16 mg/mL glycerin, and zinc oxide. The insulin analog-zinc crystals contained about 0.36% zinc on a weight basis. The concentration of zinc oxide in the aqueous diluent was such as to supplement the final zinc ion concentration of the formulation to about 0.025 mg per 100 units of insulin activity. A volume of 10% hydrochloric acid was added to adjust the pH to 2.8 to 3.0. After stirring to dissolved the crystals, aliquots of 10% sodium hydroxide solution were carefully added to adjust the pH to 7.4 to 7.7. A volume of a stock solution of TRIS (50 mg/mL, pH 7.4, measured at ambient temperature, i.e., about 22° C.) calculated to give a concentration of TRIS of 2 mg/mL in the final formulation was added to the insulin analog solution. Water was added to dilute the formulation to the final volume. The formulation was sterile-filtered using a 0.2 micron filter.

EXAMPLE 4

Preparation of a U400 Soluble Formulation Containing $Lys^{B28}Pro^{B29}$-Human Insulin Analog and Phosphate An amount of $Lys^{B28}Pro^{B29}$-Human Insulin Analog-Zinc Crystals calculated to yield 400 Units of insulin activity per milliliter in the final formulation were suspended in an aqueous solution containing 0.715 mg/mL phenol, 1.76 mg/mL m-cresol 16 mg/mL glycerin, and zinc oxide. The insulin analog-zinc crystals contained about 0.36% zinc on a weight basis. The concentration of zinc oxide in the aqueous diluent was such as to supplement the final zinc ion concentration of the formulation to about 0.025 mg per 100 units of insulin activity. A volume of 10%; hydrochloric acid was added to adjust the pH to 2.8 to 3.0. After stirring to dissolve the crystals, aliquots of low sodium hydroxide solution were carefully added to adjust the pH to 7.4 to 7.7. A volume of a stock solution of dibasic sodium phosphate calculated to give a concentration of dibasic sodium phosphate of 3.78 mg/mL, pH 7.4±0.1 in the final formulation was added to the insulin analog solution. Water was added to dilute the formulation to the final volume. The formulation was sterile-filtered using a 0.2 micron filter.

EXAMPLE 5

Preparation of a U400 Soluble Formulation Containing $Lys^{B28}Pro^{B29}$-Human Insulin Analog and L-Arginine The process described in Example 3 was followed until addition of the buffer. Then, instead of adding a volume of a TRIS stock solution, a volume of a stock solution of L-arginine (200 mM, pH 7.4) calculated to give a concentration of L-arginine of 20 mM in the final formulation was added to the insulin analog solution. Water was added to dilute the formulation to the final volume. The formulation was sterile-filtered using a 0.2 micron filter.

EXAMPLE 6

Preparation of U100 $Lys^{B28}Pro^{B29}$-Human Insulin Analog High Mixture Formulation (75% v/v soluble, 25% v/v Neutral Protamine $Lys^{B28}Pro^{B29}$) Containing L-Arginine A. Preparation of Neutral Protamine $Lys^{B28}Pro^{B29}$ An amount calculated to contain 200 U/mL of $Lys^{B28}Pro^{B29}$ Zinc Insulin Crystals was suspended in an aqueous solution containing 0.715 mg/mL phenol, 1.76 mg/mL m-cresol, 16 mg/mL glycerin, and zinc oxide acidified with hydrochloric acid so as to supplement the final zinc ion concentration to 0.025 mg/100 U. A volume of 10% hydrochloric acid was added to adjust the solution to pH 2.8 to 3.0. After stirring to dissolve, 10% sodium hydroxide solution was added to adjust the solution to pH 7.4 to 7.7. A volume equivalent to a final 3.78 mg/mL formulation concentration of 75.6 mg/mL dibasic sodium phosphate solution at pH 7.2 was added. Following dissolution of the precipitated solids and titration to maintain pH 7.4, water was added to dilute the formulation to final volume, after which the solution was filtered.

Solid protamine sulfate, calculated to containing 0.6 mg/100 U protamine base, was dissolved in an aqueous solution containing 0.715 mg/mL phenol, 1.76 mg/mL m-cresol and 16 mg/mL glycerin. Solid dibasic sodium phosphate was added so that the formulation concentration was 3.78 mg/mL. The solution was adjusted to pH 7.4 with 10% hydrochloric acid, diluted to final volume with water, and filtered.

Both the 200 unit $Lys^{B28}Pro^{B29}$ solution and the protamine solution were equilibrated at 15° C. The protamine solution was added to the $Lys^{B28}Pro^{B29}$ solution and the resulting suspension allowed to incubate undisturbed at 15° C. for 24 hours.

B. Preparation of $Lys^{B28}Pro^{B29}$ High Mixture

An amount of $Lys^{B28}Pro^{B29}$ 100 unit solution containing L-arginine prepared in Example 2 corresponding to 75% of the final volume was added to a calculated volume of 100 U/mL neutral protamine $Lys^{B28}Pro^{B29}$. The suspension was stirred at ambient temperature.

EXAMPLE 7

Preparation of U100 Lys$^{B28}$Pro$^{B29}$-Human Insulin Analog Low Mixture Formulation (25% v/v soluble, 75% v/v Neutral Protamine Lys$^{B28}$Pro$^{B29}$) Containing L-Arginine A. Preparation of Neutral Protamine Lys$^{B28}$Pro$^{B29}$ An amount calculated to contain 200 U/mL of Lys$^{B28}$Pro$^{B29}$ Zinc Insulin Crystals was suspended in an aqueous solution containing 0.715 mg/mL phenol, 1.76 mg/mL m-cresol, 16 mg/mL glycerine and zinc oxide acidified with hydrochloric acid so as to supplement the final zinc ion concentration to 0.025 mg/100 U. A volume of 10% hydrochloric acid was added to adjust the solution to pH 2.8 to 3.0. After stirring to dissolve, 10% sodium hydroxide solution was added to adjust the solution to pH 7.4 to 7.7. A volume equivalent to a final 3.78 mg/mL formulation concentration of 75.6 mg/mL dibasic sodium phosphate solution at pH 7.2 was added. Following dissolution of the precipitated solids and titration to maintain pH 7.4, water was added to dilute the formulation to final volume, after which the solution was filtered.

Solid protamine sulfate, calculated to contain 0.6 mg/100 U protamine base, was dissolved in an aqueous solution containing 0.715 mg/mL phenol, 1.76 mg/mL m-cresol and 16 mg/mL glycerin. Solid dibasic sodium phosphate was added so that the formulation concentration was 3.78 mg/mL. The solution was adjusted to pH 7.4 with 10% hydrochloric acid, diluted to final volume with water, and filtered.

Both the U200 Lys$^{B28}$Pro$^{B29}$ solution and the protamine solution were equilibrated at 15 C. The protamine solution was added to the Lys$^{B28}$Pro$^{B29}$ solution and the resulting suspension allowed to incubate undisturbed at 15 C. for 24 hours.

B. Preparation of Lys$^{B28}$Pro$^{B29}$ Low Mixture

An amount of Lys$^{B28}$Pro$^{B29}$ U100 solution containing L-arginine prepared in Example 2 corresponding to 25% of the final volume was added to a calculated volume of 100 U/mL neutral protamine Lys$^{B28}$Pro$^{B29}$. The suspension was stirred at ambient temperature.

We claim:

1. A solution formulation comprising: a physiologically tolerated buffer selected from the group consisting of TRIS and arginine; a monomeric insulin analog; zinc; and a phenolic preservative, wherein the formulation is a solution formulation.

2. The formulation of claim 1 wherein the buffer is TRIS.

3. The formulation of claim 2, wherein the monomeric insulin analog is AspB28-human insulin.

4. The formulation of claim 2 further comprising an isotonicity agent and wherein the pH of the formulation is between pH 7.0 and pH 8.0 when measured at a temperature of 22° C.

5. The formulation of claim 4, wherein the monomeric insulin analog is AspB28-human insulin.

6. The formulation of claim 5, wherein the concentration of AspB28-human insulin is between about 1.2 mg/mL and about 50 mg/mL.

7. The formulation of claim 6, wherein the concentration of AspB28-human insulin is between about 3.0 mg/mL.

8. The formulation of claim 7, wherein the concentration of AspB28-human insulin is between about 3.5 mg/mL.

9. The formulation of claim 8, wherein the concentration of AspB28-human insulin is between about 7 mg/mL.

10. The formulation of claim 9, wherein the concentration of AspB28-human insulin is between about 14 mg/mL.

11. The formulation of claim 10, wherein the concentration of AspB28-human insulin is between about 17.5 mg/mL.

12. The formulation of claim 4, wherein the phenolic preservative is a mixture of m-cresol and phenol.

13. The formulation of claim 12, wherein TRIS is present at a concentration of about 2 mg/mL; glycerol is the isotonicity agent and is present at a concentration of about 16 mg/mL; and wherein m-cresol is present at a concentration of about 1.76 mg/mL and phenol is present at a concentration of about 0.715 mg/mL.

14. The formulation of claim 13, wherein the monomeric insulin analog is AspB28-human insulin.

15. A stable, soluble formulation of a monomeric insulin analog, for use in a continuous infusion system, consisting essentially of: an isotonicity agent; a buffer selected from the group consisting of TRIS and arginine; zinc; and a phenolic preservative.

16. The formulation of claim 15, wherein the monomeric insulin analog is AspB28-human insulin.

17. The formulation of claim 1, wherein the buffer is arginine and the formulation further comprises protamine.

18. A method for treating diabetes comprising administering an effective dose of the formulation of claim 1 to a patient in need thereof.

19. The method of claim 18, wherein the formulation is administered using a continuous infusion system.

20. A method for treating hyperglycemia comprising administering an effective dose of the formulation of claim 1 to a patient in need thereof.

21. The method of claim 20, wherein the formulation is administered using a continuous infusion system.

22. A method for treating diabetes comprising administering an effective dose of the formulation of claim 17 to a patient in need thereof.

23. A method for treating hyperglycemia comprising administering an effective dose of the formulation of claim 17 to a patient in need thereof.

* * * * *